(12) United States Patent
Veronesi et al.

(10) Patent No.: US 7,012,062 B2
(45) Date of Patent: Mar. 14, 2006

(54) USE OF MODIFIED LYSOZYME C TO PREPARE MEDICINAL COMPOSITIONS FOR THE TREATMENT OF SOME SERIOUS DISEASES

(75) Inventors: Paolo Alberto Veronesi, Milan (IT); Paolo E. A. Rodriguez, Cordoba (AR)

(73) Assignee: Therapicon SRL, Milan (IT)

( * ) Notice: Subject to any disclaimer, the term of this patent is extended or adjusted under 35 U.S.C. 154(b) by 241 days.

(21) Appl. No.: 10/227,314

(22) Filed: Aug. 26, 2002

(65) Prior Publication Data

US 2003/0124110 A1   Jul. 3, 2003

Related U.S. Application Data

(63) Continuation of application No. 09/674,301, filed as application No. PCT/IT99/00142 on May 20, 1999, now abandoned.

(30) Foreign Application Priority Data

May 22, 1998  (IT) ........................... MI98A001148

(51) Int. Cl.
*A01N 37/18* (2006.01)
(52) U.S. Cl. ........................................ 514/2
(58) Field of Classification Search ............... 514/2
See application file for complete search history.

(56) References Cited

U.S. PATENT DOCUMENTS

| | | | |
|---|---|---|---|
| 5,382,657 A | 1/1995 | Karasiewicz et al. | |
| 5,711,944 A | 1/1998 | Gilbert et al. | |
| 5,880,255 A | 3/1999 | Delgado et al. | 530/303 |
| 5,908,621 A | 6/1999 | Glue et al. | |
| 6,177,074 B1 | 1/2001 | Glue et al. | |

FOREIGN PATENT DOCUMENTS

WO   94/01127   1/1994

OTHER PUBLICATIONS

Takada et al, "Binding of Lysozyme to Lipopolysaccharide . . . ," Infection and Immunity, vol. 62, No. 4, pp. 1171-1175 (1994).
Sava et al, "Mechanism of the Antieoplastic Action of Lysozyme . . . ," Anticancer Research, vol. 9, pp. 1175-1180 (1989).
So et al, "Reduced immunogenicity of monomethyoxypolyethylene . . . ," Immunology Letters, vol. 49, p. 91-97 (1996).
Pacor et al, "Antimetastatic Action and Lymphocyte Activation . . . ," Anticancer Research, vol. 16, pp. 2559-2564 (1996).
Protein Homology Search (Swiss-Prot); Oct. 13, 1995; 2pp.
Yuji Inada et al; "Application of polyethylene glycol-modified enzymes in biotechnological processes: organic solvent-soluble enzymes"; TIBTECH; Jul. 1986; pp. 190-194.
Yuji Inada et al; "Biomedical and biotechnological applications of PEG- and PM-modified proteins"; TIBTECH; Mar. 1995 (vol. 13); pp. 86-91.
Francesco M. Veronese; "Peptide and protein PEGylation: a review of problems and solutions"; Biomaterials; 22 (2001); Elsevier Science Ltd.; pp. 405-417.

*Primary Examiner*—Michael Meller
(74) *Attorney, Agent, or Firm*—Buchanan Ingersoll, P.C

(57) ABSTRACT

Use of modified lysozyme c or its pharmaceutically acceptable salts and its industrial production for the preparation of medicinal compositions, suitable for oral, parenteral and topical administration, for prophylaxis and therapy of diseases in mammals.

6 Claims, No Drawings

USE OF MODIFIED LYSOZYME C TO PREPARE MEDICINAL COMPOSITIONS FOR THE TREATMENT OF SOME SERIOUS DISEASES

This application is a continuation of application Ser. No. 09/674,301, filed Dec. 11, 2000, now abandoned, the entire content of which is hereby incorporated by reference in this application, application Ser. No. 09/674,301 being the U.S. national stage of International Application No. PCT/IT99/00142, filed May 20, 1999.

This invention relates to the use of modified lysozyme c compound or to its pharmaceutically acceptable addition salts and to its industrial production for the preparation of medicinal compositions, more particularly oral, parenteral and topical, for prophylaxis and therapy of some serious diseases in mammalians.

BACKGROUND OF THE INVENTION

It is known that natural lysozyme is an enzyme of peptidic origin, widely present in many species of the animal and vegetal world, having in the different species comparable but not identical structure and enzymatic mechanism. The most known lysozyme is that present in the chicken egg (chicken egg-white lysozyme c). Lysozyme is widely distributed in the mammalians body; it is present for example in saliva, in tears, in milk, in leukocites, in cervical mucus. In 1922 Alexander Fleming discovered a substance present in his own nasal mucus able to lysate some bacterial strains. This substance has been later on identified as lysozyme (today better identified as human lysozyme c). In 1963 Jolles and Canfield independently clarified the primary structure of lysozyme purified from chicken egg-white. In 1965 Phillips describes the tridimensional structure of lysozyme, on the basis of the X-rays crystallography. As from its discovery, natural lysozyme (more precisely the chicken egg-white lysozymne c) has been used sometimes in medicine mainly for its anti-bacterial properties, but the retrospective analysis of the published studies has not even today fully clarified its specific mechanism of action and in some cases the experimental results seem to be even contradictory (1,2,3).

Nowdays scientists think that the biological action of natural lysozyme c shall be divided in two different ways: a direct action and an indirect action. The direct action is determined by the degradation of the link ($\beta$, 1-->4) between N-acetylmuramic acid and N-acetylglucosamine (4) of peptidoglycanes present in the cell membrane of bacteria, thus determining the lysis of the same (as consequence of this action it is frequently called "muramidase"). Generally Gram positive bacteria are more sensitive to natural lysozyme's action than Gram negative, probably because the latter ones present the external membrane, as further barrier. This direct action of lysozyme is potentially important for its possible therapeutic use in prophylaxis and treatment of many bacterial diseases, alike faringitis, congiuntivitis, otitis, sinusitis, adenitis, uretritis, vaginitis, cistitis, substantially caused by microorganisms of Streptococci family. By contrast, the degradated mucopeptidic fragments of the cell membrane, produced by the direct action of lysozyme on the bacteria, seem to be able to elicit a not well defined process of immunological stimulation (indirect action of lysozyme).

Some authors have also recently described the capacity of chicken egg-white lysozyme c and of its derivatives to stimulate the production of lymphocytes T present in the lymphatic tissue, associated to intestine (GALT), and in spleen (GALT-speen axis).

However in literature some authors have also described the use of other specific lytic peptides for the treatment of many diseases. In some recent patents the specific combination of the administration of Cecropins and lysozyme has been suggested, in order to increase the action of the two compounds. In fact some authors suggest that Cecropins are much more active in lysing the cell, while lysozyme is more active in its complete degradation.

The new chemotherapeutic agents, like Cecropins, Sarcotoxins, Magainins, Lepidopterans, having the same physical properties with an $\alpha$-elique structure and hydrophobic character, are proteins able to lysate not only the cellular membrane of bacteria (*Listeria monocitogenes* and *Brucella abortus*), but also the cell membrane of protozoos (*P. Falciparum*) and viruses (Parainfluenza and Herpes Simplex), and of eukariotes cells infected with bacteria. By using an electronic microscope it has been discovered that lytic peptides produce large pores into membrane of cells, determining their death. By contrast, healthy mammalian cells are not destroyed by the above lytic peptides, due probably to the presence of citoskeleter, which is in contact with various points of the plasmatic membrane and consequently it permits to maintain the osmotic integrity of the cell.

Moreover also at low concentrations the lytic peptides shall be used as biological response modifiers, in order to stimulate the cells proliferation of the immunological system and of the skin. The above action is probably caused by the production of pores in the plasmatic membrane, determining a flow of ions and of nutritive material into the cells, which stimulates the cells' growth.

Nevertheless, although many publications evidence the positive action of natural lysozyme (mainly chicken egg-white lysozyme c) in the treatment of infections of various origin, the potential use of group c lysozyme in clinics has been very limited until nowadays due to three major factors:

a) human lysozyme c (which is the type present in humans) is extremely difficult to be obtained in sufficiently large amounts for therapeutic applications;

b) other lysozyme c types, which are obtainable from other species, alike bovine and chicken egg-white, may present some negative side-effects (the first one is possible allergic reactions and the second one is the potential risk of contamination of transmissible bovine encephalopathies or TBE), which are considerably limiting their use in medicine;

c) lysozyme types, different from c, originating from other animal species are not suitable for medicinal purposes since they present a very low homology with human lysozyme c.

A table is reported wherein the homology between human lysozyme and lysozymes from other mammalians, however all of natural c type, is indicated:

| LYSOZYME ORIGIN | HOMOLOGY % |
| --- | --- |
| Egg (white) chicken | 56.8% |
| Rat | 76.4% |
| Cow | 82.3% |
| Rabbit | 82.3% |
| Horse | 50.8% |

Although bovine lysozyme c shows an homology higher than that of chicken egg-white, the latter one is the most used in the clinical practice due that it is very commonly available in suitable quantities at convenient prices. On the basis of the above introduction there is a considerable interest to further explore new possibilities of use of natural lysozyme c, of its possible derivatives and to produce medicinal preparations, which permit to widen its use to some serious diseases in humans and/or to utilize new and previously unexplored administration routes.

Despite many experimental researches on animals and recent publications on lysozyme c, the medicinal applications of this compound when administered orally remained limited to traditional pathologies, already well known to the experts.

However these studies seem to have achieved very limited and sometimes contrasting results.

DESCRIPTION OF THE INVENTION

Therefore the main purpose of present invention is to provide medicinal compositions containing a modified natural lysozyme c compound, more particularly a monomethoxypolyethylene glycol lysozyme c compound (hereinafter defined as <<MLc>> for practicalness of the description) or its addition salts with pharmaceutically acceptable acids, presenting the following general formula (I):

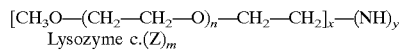
Lysozyme c.(Z)$_m$ wherein:

y=number of free amino groups of molecules of lysine present in the molecule of lysozyme c, preferably comprised between 5 and 30;

x=number of molecules of monomethoxypolyethylene glycol for each molecule of lysozyme c, where the value may vary from 1 to y;

n=number of polymerization degree of polyethylene glycol portion, preferably comprised between 5 and 1000;

Lysozyme c=lysozyme c from chicken egg-white, rat, cow, rabbit, horse or human;

Z=pharmaceutically acceptable organic or inorganic acid, monovalent or polyvalent, able to produce addition salts with the considered lysozyme c;

m=number of molecules of pharmaceutically acceptable acid used for the obtention of MLc addition salt, which may vary from 0 to the value corresponding to total number of amino groups present in the molecule of lysozyme c.

This compound is surprisingly and particularly useful and effective for the specific treatment of some serious diseases in mammalians.

More particularly in the modified lysozyme c compound, utilized as active ingredient for the preparation of medicinal compositions useful for the treatment of some serious diseases in mammalians, the number of radicals of monomethoxypolyethylene glycol (x) may vary from 1 to "y", the polymerization degree (n) of the polyethylene glycol portion of monomethoxypolyethylene glycol shall be comprised between 5 (M.W. about 161) and 1,000 (M.W. about 32,206), more preferably between 120 (M.W. 3,865) and 200 (M.W. 6,441), while the number of molecules of the amino acid lysine (y), having a —NH— radical linked with monomethoxypolyethylene glycol, in lysozyme c may vary from 5 (human and chicken egg-white), to 11 (bovine) or even more, to a maximum of 30.

Z means any pharmaceutically acceptable organic or inorganic acid, mono or polyvalent, pharmaceutically acceptable, which may be combined in different fashion, being "m" the number of molecules of the pharmaceutically acceptable acid, which may be required to yield addition salt with MLc and which may vary from 0 to the value corresponding to the total number of amino groups present in the molecule of the considered lysozyme c, value which shall be divided by the valence of the same acid (Z).

Recently some authors have published that generally proteins can produce, by quite simple chemical reactions already known to the artisans skilled in the art, derivatives of condensation with polyethylene glycols.

Therefore also the chicken egg-white lysozyme c may produce, by reacting with monomethoxypolyethylene glycol (polymerization degree n comprised between 5 and 1000) or with its activated derivative (tresylated monomethoxypolyethylene glycol), with a reaction providing a direct linkage between the polymer and the protein via a stable secondary amine, the pegilated derivative of chicken egg-white lysozyme c.

At the present state of the art pegilated derivatives of other lysozymes of c group are unknown, and therefore they shall be considered not described and novel, as also their therapeutic use.

It has been also observed that these pegilated derivatives present generally a reduced immunoreactivity and a better stability against heating and degradation during their storage. Some authors have also formulated the hypothesis that these pegilated derivatives could show, after their absorption, also a better resistance to the proteolytic agents and therefore a better half-life in plasma.

These pegilated derivatives can be also obtained by a synthesis process which determines a covalent binding of the selected natural lysozyme c with the selected monomethoxypolyethylene glycol radicals, after exposing at room temperature during about 2 hours lysozyme c to tresylated monomethoxypolyethylene glycol in PBS (Phosphate Buffer Saline) or in a borate buffer at different pH (almost always in slightly basic medium) and in different proportions. The tresylated glycol reagent may be commonly obtained from monomethoxypolyethylene glycol activated with tresyl chloride. Monomethoxypolyethylene glycol is selected to provide only one reactive end in each molecule, thus avoiding undesired cross-linked products, but yielding only the desired MLc selected compound. The purification of MLc is carried out using Shepadex G-50 columns (12 cm×1.3 cm) stabilized with PBS, or by ultracentrifugation with Amicon membranes of desired porosity. In case it is desired to obtain the addition salts of MLc, for example MLc hydrochloride, it is necessary to carry out a dialisis with an aqueous solution of diluted HCl (10–100 mM) for all night at 4° C. or more preferably for 6–8 hours at room temperature, then carrying out the purification by Sephadex G-50 column. The resulting salt shall be then lyophilized and stored at temperatures below 0° C., until to be used.

A possible general synthesis scheme of addition salts of MLc are indicated herebelow, for a better understanding of their synthesis process (NOTE: the amino groups of lysozyme c are evidenced for a better understanding):

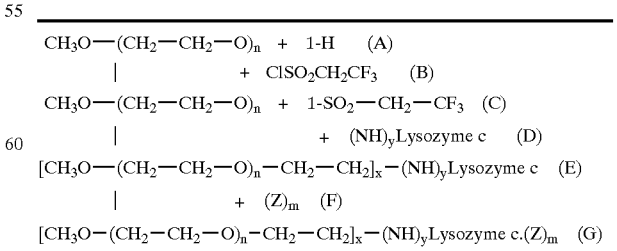

A = monomethoxypolyethylene glycol (MPEG) with only one final reactive group;

-continued

B = tresyl chloride (2,2,2-trifluoroethane-sulfonyl-chloride);
C = tresylated monomethoxypolyethylene glycol (TMPEG);
D = lysozyme c;
E = modified lysozyme c (MLc);
F = pharmaceutically acceptable acid;
G = MLc addition salt.

Protein concentrations are then measured directly by determining the absorbance at 280 nm and by "Coomassie brilliant blue" titration. For the colorimetric reaction 100 μl of the protein sample is aliquoted in microtiter plates and 200 μl of "Coomassie protein assay" reagent are added. The absorbance at 555 nm is measured by means of a microtiter reader after 5 minutes of incubation at room temperature. By using both the described methods, the concentration of the samples is established by means of a calibration curve obtained from a stock solution of lysozyme c at a known concentration.

The obtained MLc is then tested by determining the assay using three different methods: 1) SDS-Polyacrilamide gel electrophoresis; 2) Molecular filtration chromatography; 3) Enzymatic activity according to the conventional method.

1) SDS-Polyacrylamide Gel Electrophoresis

A 15% polyacrylamide gel is used. The running is usually carried out between 100 and 150 V, for about 45 minutes.

Concentrated Solution of Acrylamide (30%)/Bisacrylamide:

Dissolve 29.2 g of acrylamide and 0.8 g of bisacrylamide in 70 ml of deionized water. Once acrylamide is dissolved, add water to yield a volume of 100 ml. Filtre the solution through a 0.45 μm pore size membrane. The obtained solution is stable at 4° C. for 1 month when stored in a dark bottle.

Buffer A (1.5 M Tris-HCl Buffer, pH 8.80):

Dissolve 18.2 g of Tris base in about 80 ml of distilled water. Adjust the pH to 8.80 with HCl and yield 100 ml volume adding distilled water. Store the obtained Buffer A at 4° C.

Buffer B (0.5 M Tris-HCl Buffer, pH 6.80):

Dissolve 6.1 , of Tris base in 80 ml of distilled water. Adjust the pH to 6.80 with HCl and yield 100 ml volume adding distilled water. Store the obtained Buffer B at 4° C. 10% (w/v) sodium dodecylsulphate (SDS):

Dissolve 10 g of SDS in 60 ml of water. Bring to 100 ml volume with distilled water.

Dissolution Buffer of the Sample (0.06 M Tris-HCl, pH 6.80. 2% SDS, 10% Glycerol, 0.025% Bromophenol Blue)

| Water | 4.80 ml |
| Buffer B | 1.20 ml |
| SDS 10% | 2.00 ml |
| Glycerol | 1.00 ml |
| Bromophenol blue 0.5% | 0.50 ml |

Store the above solution at room temperature. The SDS-reducing buffer is prepared adding 50 μl of 2-mercaptoethanol to each 0.95 ml of buffer solution of the sample. Prepare this solution at the moment of its use.

Catalyst (10% w/v Ammonium Persulphate):

Dissolve 100 mg of ammonium persulphate in 1 ml distilled water. Prepare this solution at the moment of its use.

TEMED:

Use directly the product present in the bottle. Store in a not wet place, protected from light.

Elution Buffer (0.025 M Tris, 0.192 M Glycerol, 0.1% (w/v) SDS pH 8.30±0.20):

Dissolve 0.3 g of Tris base, 1.4 g of glycerol, 1 ml of 10% SDS in 100 ml distilled water. Store this elution buffer at 4° C.

Preparation of 15% Polyacrylamide Gel (0.375 M Tris, pH 8.80):

| Distilled water | 2.35 ml |
| Buffer A | 2.50 ml |
| 10% SDS (w/v) | 0.10 ml |
| Concentrated solution of: | |
| 30% acrylamide/bisacrylamide | 5.00 ml |
| 10% (w/v) ammonium persulphate | 0.05 ml |
| TEMED | 0.005 ml |
| Total volume | 10.005 ml |
| Preparation of 4% polyacrylamide gel (0.125 M Tris, pH 6.80): | |
| Distilled water | 6.10 ml |
| Buffer B | 2.50 ml |
| 10% SDS (w/v) | 0.10 ml |
| Concentrated solution of: | |
| 30% acrylamide/bisacrylamide | 1.30 ml |
| 10% (w/v) ammonium persulphate | 0.05 ml |
| TEMED | 0.005 ml |
| Total volume | 10.055 ml |

Sample Preparation:

Dilute the sample with 4 volumes of reducing-SDS buffer and heat to 95° C. for 4 minutes (each band of the gel shall contain not less than 1 μg of protein). The electrophoretic migration is carried out by using a MiniProtean II (BioRad, California) equipment, at room temperature. The applied voltage is 100–150 V for about 45 minutes.

Gel Coloration with Coomassie Brillant Blue R-250:

Dissolve 0.2 g of Coomassie brillant blue R-250 in 1 liter of a solution containing 50% (v/v) of methanol, 10% (v/v) of acetic acid and 40% (v/v) of distilled water. Filtre the solution using a filtering paper and store the solution in an ambered bottle. Before using the obtained solution, it is necessary to check always if a coloured precipitate is present. In affermative case filtre again.

Place the gel during 10 minutes in a solution containing 50% (v/v) of methanol, 10% (v/v) of acetic acid and 40% (v/v) of distilled water in order to eliminate the presence of SDS.

Keep the gel in the coloured solution under constant and slow stirring during 30 minutes at 50° C. or alternatively during two hours at room temperature.

Preserve the gel in a liquid medium consisting from a 10% (v/v) acetic acid solution. Alternatively dry the gel using a glycerol solution and a cellophane film and proceed in the following way:

a) place the gel for 10–15 minutes in a 10% (v/v) glycerol solution; b) wet the cellophane film in the same solution, c) place the gel between two wetted cellophane films without introducing air bubbles; d) place the gel on a shelf and leave it at room temperature.

Evaluation of the Results:

The sample composition is determined by densitometry at 595 nm on the gel, using a suitable equipment, as for example Shimadzu UV/VIS CS 930 scanner.

Acceptability Limit:

The sample shall contain a single spot, after coloration by Coomassie brillant blue R-250.

MLc content shall not be less than 95%.

2) Molecular Filtration Chromatography

The sample is chromatographied using a Superose 12HR 10/30 column and an equipment for FPLC (Fast Performance Liquid Chromatography) equilibrated with PBS. The sample is diluted with PBS before loading it on the column. Inject 200 µl of the sample and elute with PBS at a flow rate of 0.3 ml/min. Collect fractions of 0.25 ml. The elution profile is determined by spectrophotometry at 280 nm. The proteic concentration is determined quantitatively by using Coomassie brillant blue. Use markers with known molecular weight at a concentration of 3 mg/ml, as for example β-amilase (200 KDa), alcohol dehydrogenase (150 KDa), bovine serum albumine (66 KDa), carbonic anhydrase (29 KDa), citochrome C (12.4 KDa), aprotinine (6.5 Kda). MLc lutes at about 17.35 ml under the indicated conditions.

Acceptability Limit:

MLc content shall not be less than 95%.

3) Enzymatic Activity

This method is carried out according to the conventional methods already described in literature (5, 6, 7).

Test Conditions:

A) Suspension of *Micrococcus luteus* (*Micrococcus lysodeikticus*) at a concentration of 3 mg/ml in 0.2 M phosphate buffer (pH=7.00) and 17 mM of NaCl.

B) Solution of MLc (1 mg/ml) in distilled water.

C) Spectrophotometer suitable to determine absorbance variations at 450 nm.

Procedure

Place 2.9 ml of a *Micrococcus luteus* (*Micrococcus lysodeikticus*) suspension in a spectrophotometric cuvette. Leave the suspension for 4–5 minutes at 25° C., in order to allow the suspension to reach the reaction temperature. Add 0.1 ml of enzymatic solution and record the absorbance variation each minute at 450 nm.

Calculation of Enzymatic Activity of MLc:

$$\text{Units/mg} = \frac{(\Delta A_{450 \text{ nm}}/\text{min}) \times 10^3}{\text{mg of enzyme in the reaction mixture}}$$

Enzymatic unit is defined as the enzyme quantity, which in the test conditions (pH=7.00 at 25° C.) decreases of 0.001 each minute the absorbance of Micrococcus luteus suspension. Therefore the above demonstrates that MLc maintains also the main enzymatic activity, already known in natural lysozyme c.

In another embodiment of the instant invention the authors have surprisingly noticed that the administration route of MLc or its pharmaceutically acceptable salts is fundamental and determinant in order to elicit unknown and remarkable therapeutic effects on some severe diseases in mammalians.

In fact the authors have surprisingly discovered that oral administration of MLc may induce high plasmatic levels of free TNF-α (Tumor Necrosis Factor alpha), biologically available, thus inhibiting by a practically direct mechanism and significantly the replication speed of the tumoral proliferative process in mammalians (8, 9, 10). In fact an embodiment particularly preferred of the present invention is the use of MLc for the preparation of medicinal compositions to be administered by oral route or, that in another way, the oral administration of MLc is suitable to induce a significant plasmatic increase of free TNF-α, resulting this last substance, when biologically available, particularly useful for its protective effect and for the specific treatment of tumoral processes in general, especially when all at the initial stage.

It is in fact known from the most recent publications that TNF-α is a specific factor, as indicated by its name, able to induce the inhibition, however the necrosis, of the tumoral process of the cells also when grown in vitro.

The tumoral processes are paradoxically accompanied by high haematic levels of TNF-α, which is linked to soluble forms of receptors and therefore it is not free and biologically available. On the contrary it is very important to induce high levels of free TNF-α (11, 12, 13). The mechanism why MLc only by oral administration is able to remarkably induce the increase of the plasmatic levels of free TNF-α is still unknown, being still matter of research by the authors, but it can be hypothetically related in vivo to a possible active stimulation of the biosynthesis process of TNF-α. The mechanism can be explained in the way that the gene transcription of TNF and mRNA translation are both strongly stimulated by peptidoglycans, which are the most direct and significant expression of the enzymatic and lytic activity of MLc, administered by oral route, on cell walls of bacteria, normally components of intestinal flora (14), thus demonstrating by contrast that MLc has maintained its enzymatic activity similar to that corresponding to natural lysozyme c, which is in net contradiction with the publication of other authors. Concerning the mechanism it is necessary to consider that a recent study has indicated that MAP kinase homologs become phosphorylated in peptidoglycans-stimulated cells, thus suggesting their possible involvement in signal transduction.

Most of the pleiotropic biological actions of TNF can be attributed to its ability to activate a variety of genes in a multitude of target cells. TNF-α and the functionally related cytokine IL-1 are the only natural substances known to have such a large spectrum of target gene. Partial list of proteins induced by TNF includes: IL-1α and IL-1β, IL-6, IL-8, IFN-β, IL-2 receptor α chain and many others.

Surprisingly the authors have also noted in the instant invention that the oral administration of MLc decreases also the plasmatic levels of sialic acid (total), which is an "aspecific marker", which increases pathologically in some serious degenerative processes, including different types of tumors. The above finding further supports that free TNF-α stimulation, obtained from oral administration of MLc, determines, as claimed, therapeutic inhibition effects of neoproliferative processes, which are expression of tumoral cells in animals. Therefore one may conclude that the first objective of the present invention is the use of MLc or its pharmaceutically acceptable salts for the preparation of medicinal compositions to be administered only by oral route in order to obtain a remarkable increase of plasmatic level of free TNF-α, thus bioloqically available, and consequently particularly useful in the prophylaxis and treatment of tumoral processes in mammaliaris, for which an increase of plasmatic free TNF-α (not blocked by soluble forms of receptors) is able to produce beneficial and therapeutic effects.

Other preferred and important embodiment of the present invention is the use of MLc or of its pharmacologically acceptable salts for the preparation of medicinal compositions particularly useful for the treatment of rheumatoid arthritis, Acquired Immuno Deficiency Syndrome, more commonly known with the Anglo-Saxon terminology "AIDS", psoriasis and septic shock, where the most preferred administration route, to elicit the desired pharmacological and therapeutical effects, is the parenteral route, more precisely the intravenous route. In fact it has been experimentally supported that, when MLc is administered by parenteral route, more preferably by intravenous route, strongly inhibits the TNF-α plasmatic levels, thus surprisingly inducing a pharmacological response, which is just opposite to that achieved when MLc is administered by oral route.

The main target of the chronic inflammatory response in rheumatoid arthritis (RA) is the synovium. Even though it is unknown what causes this desabling disease, characterization of the infiltrated inflammatory cells and their products is of great importance to understanding its pathogenesis.

There is considerable evidence involving TNF-α in the pathogenesis of RA. This evidence is based not only on the generalized presence of TNF-α in arthritic joints, accompanied by an increased response of TNF-α receptors, but also from the effects of a neutralization of TNF-α in joint cells cultures.

Thus neutralization in vitro of TNF-α elicits the inhibition of the production of interleukin 1, as TNF-α, which is believed to be the cause determining the inflammation and the erosion of the joint.

In AIDS disease TNF-α is a potent activator of the replication of the HIV virus in the infected cells. In symptomatic patients the levels of TNF-α are higher than in asymptomatic patients. Probably TNF-α determines a transcriptional activation of HIV provirus integrated in the genoma of the host cell, by increasing the levels of viral RNA. Moreover TNF-α contributes to the viral replication, which increases in turn the destruction of $CD_4^-$ limphocytes and reduces the immunological functions of the body (15).

Consequently in the pathologies, as RA but especially AIDS, wherein the levels of TNF-a are high, the administration of MLc by oral route is not suitable, but absolutely self-defeating and contra-indicated because it may cause an exacerbation of the disease, increasing the TNF-α levels which are already very high. By contrast the present invention has surprisingly evidenced that the parenteral administration of MLc or of its pharmaceutically acceptable salts, more particularly by intravenous route in AIDS and intraarticularly in R.A, induces a remarkable and favourable therapeutic decrease of TNF-α levels in fluids (plasma in AIDS and sinovial fluid in R.A.). This important therapeutic effect, subject matter of the present invention, supports the hypothesis that the decrease of TNF-α may be attributed from the reflected inhibitory action ("rebound" effect) on cellular organs or on the mechanism at the origin of these pathologies.

Moreover an experimental significant reduction of TNF-α in plasma and in cerebrospinal fluid (CSF) were observed in non controlled studies in humans, and therefore the therapeutic indications of the medicinal parenteral preparations of MLc or its pharmacologically acceptable salts, are also particularly extended to reverse severe Central Nervous System impairment ("AIDS dementia complex" and other correlated serious motorial and cognitive disorders).

Another particularly preferred embodiment of the present invention is the use of MLc or of its pharmacologically acceptable salts for the preparation of a topical medicament, capable to elicit a remarkable antihistaminic activity, when MLc or its pharmaceutically acceptable salts are locally applied. These topical medicinal preparations of MLc or its pharmacologically acceptable salts have shown in experimental non controlled studies to prevent blood flow increase, vascular permeability, edema, pain and irritation caused by the action of histamine.

Another particularly embodiment of the present invention is that the topical medicinal preparations of MLc or of its pharmacologically acceptable salts result particularly active to determine also by transdermic route the reduction of TNF-α levels, resulting the above medicinal products particularly indicated for the treatment of reactive arthritis, rheumatoid arthritis, psoriasis arthritis and generally in those cutaneous or subcutaneous conditions where a reduction of TNF-α levels is therapeutically required. Another preferred embodiment of the present invention is that the topical preparations of MLc or its pharmacologically acceptable salts are particularly active in the topical treatment of acne and in the prevention of decayed teeth.

Another preferred embodiment of the invention is the use of MLc or its pharmaceutically acceptable salts for the preparation of medicinal products, wherein they may be associated, in different quantities and proportions, to other substances with antibacteric action, from chemical and antibiotic origin, alike semi-synthetic or synthetic penicillins, cephalosporins, macrolides, erytromycines, quinolonic derivatives, but just to mention some of the most important ones. These associations, conveniently formulated in suitable galenical preparations known to the artisans skilled in the art, are particularly useful to overcome infections or pathologies caused from bacteria, macrovirus, virus or prions, which are particularly sensitive to the synergic therapeutic effect of these associations of MLc or its derivatives.

Another preferred embodiment of the instant invention is that in non controlled studies, wherein for ethical reasons only a limited number of healthy volunteers for each indication has been admitted, the medicinal preparations of MLc or its pharmacologically acceptable salts showed surprising therapeutic effects, which cannot be explained by the present biological knowledge but which will be matter of further researches, on other serious pathologies, alike anorexia, multiple sclerosis, amiotrophic lateral sclerosis, Alzheimer disease, Parkinson, Bovine Spongiform Encephalopathy (BSE), Bovine Trasmissible Encephalopathy (TBE), Creutzfeldt-Jacob diseases, miocardic infarct, ictus, all phatologies wherein nowdays a possible involvement of bacteria, viral agents and/or infective proteic agent (prions) may be only supposed in their etiophatogenesis.

The present invention also provides a suitable pharmaceutical composition containing MLc or its pharmacologically acceptable salts, alone or associated with one or more active ingredients of the same group or with any other different medicinal substance or with a mixture thereof, prepared by using inert pharmaceutically acceptable carriers or diluents, or a mixture thereof, at solid, liquid or gas state, at room temperature.

The pharmaceutical composition of the invention containing MLc or its pharmacologically acceptable salts, may be any preparations suitable for oral route, alike tablets, with prompt or sustained release, capsules, granulate, powder, sirup, suspension or emulsion, drops, and also suitable for parenteral administration, as sterile aqueous solutions, sterile conditionned or lyophilized powder for extemporaneous preparation of sterile injectable solutions or dispersions and finally also in the form of topical preparations, alike cream, ointment, lotion, gel and medicated gauze, and transdermic plaster. The pharmaceutical composition of the invention containing MLc or its pharmaceutically acceptable salts may also comprise by systems for application by endonasal route, spray under pression or inhaler, and rectal and vaginal suppositories, tooth-paste, all prepared according to general techniques well known to the skilled artisans.

In the medicinal compositions of the invention, to be administered orally, MLc or its pharmaceutically acceptable salts are mixed alone or with other active ingredients, in suitable quantities and proportions, in a convenient pharmaceutically acceptable carrier, solid or liquid or a mixture thereof so that to produce suitable pharmaceutical forms containing the desired doses. The oral dose unit preferably contains from 5 to 80% of the active ingredient, more preferably between 40% and 60%.

Some conventional suitable inert solid carriers are for example lactose, starch, talc, microcrystalline cellulose, calcium phosphate, magnesium stearate, dextrins and/or other excipients, binders, disintegrants, diluents, lubricants, sweetening and flavouring agents, already known in the art, with or without the use of water or of another suitable auxiliary solvent.

Conventional aqueous solutions suitable for oral use of MLc or its pharmacologically acceptable salts can be prepared by dissolving the active ingredient in water or in any other suitable liquid solvent at room temperature and adding different quantities and proportions of suitable colorants, sweeteners, flavours, stabilizers, surfactants and thicknening agents, as desired.

Aqueous suspensions suitable for oral use can be prepared by dispersing the finely powdered MLc or its pharmaceutically acceptable salts in water or in any other pharmaceutical suitable carrier with suspending agents, as natural or synthetic gums, resins, methylcellulose, sodium carboxymethylcellulose and others well known in the art.

The parenteral preparations of the invention, containing MLc or its pharmaceutically acceptable salts, may be formulated according to the known art, using suitable, parenterally acceptable solvents or diluents, more particularly water with other auxiliary excipients alike sodium chloride, sugars, buffers, ethanol, polyols (glycerol, propylene glycol), preserving agents and absorption delaying agents.

The use of these agents for suitable pharmaceutically acceptable compositions of MLc or its pharmacologically acceptable salts, is already well known in the art. In fact in the medicinal compositions of the invention any conventional excipient or a mixture thereof may be included, except insofar, as any conventional media or agent incompatible with the active ingredient.

It is especially convenient to formulate the parenteral compositions of the invention in unitary dose form to simplify its administration and to achieve uniformity of dosage, alike ampoules or vials to be produced, according to the techniques already known to the skilled artisans, under sterile and aseptic conditions and packed in atmosphere of an inert gas (nitrogen) to prevent possible degradation processes.

The concentration of active ingredient, as solution or as powder to be reconstituted, may vary from 0.5% to 10%, preferably from 2% to 4%. The preparations of the invention for topical or local use, are produced with conventional techniques already known to skilled artisans, suitable for the preparation of these pharmaceutical forms to be applied locally on the skin at therapeutically effective dosages.

When the medicinal preparations of the invention are used for oral administration, each oral unit dose may contain a quantity of MLc or its salts varying from 50 mg to 2000 mg, preferably from 250 to 1000 mg (or every 5 ml in case of liquid forms), while in case of preparations to be used parenterally the unit dose may contain from 100 mg to 2000 mg in 50 ml, preferably from 500 mg to 1000 mg, independently that the active ingredient is already dissolved in a solution or conditionned or lyophilized powder to be reconstituted with 50 ml of solvent. For topical preparations of the invention the content of the compound of formula (I) may be used at a variable concentration comprised between 0.5% and 10%, preferably between 1% and 5% of the total content.

When the oral administration is adopted, therapeutic daily doses of MLc or its salts comprised between 150 mg and 6 g a day, more preferably comprised between 500 mg and 2.5 g a day, are generally used. By parenteral route the total daily doses of MLc or its salts may vary from 200 mg to 3 g daily, preferably between 500 mg and 2 g daily. These dosages may be increased in relation to the pathology to treat, to its seriousness level and to the desired therapeutic response. Also the duration of the treatment may vary considerably, always in relation to the desease to treat, to its seriousness and to the therapeutic response which is obtained during the treatment.

However it is understood that the specific dosage, the dosage frequency, the total daily dose, and overall the length of treatment can be subject to significant variations in each patient depending on a variety of factors and evaluation criteria, alike activity of the specific compound, seriousness and pathology to treat, age, body weight, general health, sex, diet, rate of excretion, drug combination, general conditions of person undergoing therapy.

REFERENCES (1) Ossermann, E. F., Klockars, M., Halper J. e Fischel, R. E. (1973). Effects of lysozyme on normal and transformed mammalian cells. Nature 243: 331–335.

(2) Rinehart, J., Jacobs, H. e Ossermann, E. (1979). Lysozyme modulation of lymphocyte proliferation. Clin. Res. 27: 305A.

(3) Lemarbre, P., Rinehart, J. J., Kay, N. E., Vesella, R. e Jacobs, H. S. (1981). Lysozyme enhances monocyte-mediated tumoricidal activity: a potential amplifying mechanism of tumor killing. Blood 58: 994–999.

(4) Chipman, D. M. e Sharon, N. (1969). Mechanism of Lysozyme action. Scienze 165: 454–465.

(5) Shugar D. (1952). Measurement of lysozyme activity and the ultra violet inactivation of lysozyme. Biochim. Biophys. Acta 8:302.

(6) Minamiura N., Yamamoto T., Fukomoto J. (1966) Agr. Biol. Chem. 30:186;

(7) Malamy M., Horecker B. L. (1964) Biochemistry 3:1894.

(8) Sava, G., Perissin, L., Zorzet, S. e Callerio C. (1986). Antineoplastic effects of egg-white lysozyme in mice bearing solid metastasizing tumors. Anticancer Res. 6: 183–186.

(9) Sava, G., Ceschia, V. e Zabuchi, G. (1988). Evidence for host-mediated antitumor effects of lysozyme in mice bearing the Mca mammary carcinoma. Eur. J. Cancer Clin. Oncol. 24 (11): 1737–1743.

(10) Sava, G., Ceschia, V K. e Pacor, S. (1989). Mechanism of the antineoplastic action of lysozyme evidence for host mediated effects. Anticancer Res. 9: 1175–1180.

(11) McIntosh, J. K., Mule, J. J., Travis, W. D. and Rosemberg, S. A. (1990). Studies of effects of recombinant human tumor necrosis factor on autochthonous tumor and transplanted normal tissue in mice. Cancer Res. 50: 2463–2469.

(12) Semenzato, G. (1990). Tumor necrosis factor: A cytokine with multiple biological activities. Br. J. Cancer 61: 354–361.

(13) Blankenstein, T., Qin, Z. H., Sberla, K., Moller, W., Rosen, H., Volk, H. D. et al. (1991). Tumor suppresion after tumor cell-targeted tumor necrosis factor alpha gene transfer. J. Exp. Med. 173: 1047–1052.

(14) Namba, Y., Hidaka, Y., Taki, K. e Morimoto, T. (1981). Effects of oral administration of lysozyme or digested cell walls on immunestimulation in guinea pig. Infect. Immunol. 31: 580–583.

(15) Vilcek, J. and Leo, T. H. (1991). Tumor necrosis factor. New insights into the molecular mechanisms of its multiple actions. J. Biol. Chem. 266 (12):7313

The invention is further described for a better understanding in the following Examples, which shall not be considered limitative of the subject matter and of claims of the instant invention.

EXAMPLES

Example 1

Evaluation of serum levels of cytokines. TNF-α, IL-1α and IL-β, IL-6 and IL-8, in CBA mice following to oral administration of MLc (chicken egg-white) hydrochloride for 7 consecutive days.

The CBA strain mice treatment was performed by oral administration of daily dosages of MLc hydrochloride (chicken egg-white) at 25–100 mg/Kg/day for 7 consecutive days (quantity expressed as equivalent of lysozyme c of chicken egg-white). The compound under testing was carefully admixed with the powdered food. The level of TNF-α, IL-1α, IL-1β, IL-6, IL-8 has been determined on day 7 by enzyme immunoassay (ELISA). Table 1 shows the obtained results, evidencing the increased level of plasmatic TNF-α and consequently of other cytokines following after administration of MLc (chicken egg-white):

TABLE 1

PLASMATIC LEVELS OF TNF-α AND CYTOKINES (pg/ml)
Following 7 days oral treatment with MLc
(chicken egg-white)

| Pre-Treatment (mg/Kg/day) | TNF-α | IL-1α | IL-1β | IL-6 | IL-8 |
|---|---|---|---|---|---|
| 0 | 6.14 | 7.16 | 1.51 | 3.52 | 2.81 |
| 25 | 11.14 | 10.74 | 2.42 | 5.24 | 4.50 |
| 100 | 11.80 | 11.07 | 2.57 | 5.63 | 4.06 |

Example 2

Evaluation of serum levels of TNF-α and IFN-α (alpha-interferon) in volunteer patients with AIDS following administration of MLc (chicken egg-white) hydrochloride by intravenous route (phleboclysis). It has been confirmed that in AIDS, TNF-α and TNF-β appear to play a crucial role, by enhancing the replication of HIV, as well as inducing their own expression and that of other cytokines. Plasmatic levels of TNF-α and IL-1 are substantially increased during AIDS progression. Consequently gaining a control over the TNT-α induction, it is possible to establish an effective therapy for AIDS.

MLc as it is or as salt inhibits the synthesis of TNF-α and stimulates simultaneously the synthesis of IFN-α

In views of the above considerations 20 mg/Kg/day of MLc hydrochloride (quantity expressed as equivalent of chicken egg-white lysozyme c) was administered by slow intravenous route to healthy controls, HIV-infected patients and HIV-infected asymptomatic patients during "n" consecutive days (n=not less than 120 days). Table 2 shows the obtained results, confirming a reduction of TNF-α plasmatic level and an increase of IFN-a following administration of MLc (chicken egg-white) hydrochloride:

TABLE 2

| | Number | TNF-α Plasmatic | IFN-α Plasmatic |
|---|---|---|---|
| Control | 20 | 10.30 | 1.60 |
| HIV-infected patients symptomatic | 15 | 20.09 | <1 |
| asymptomatic | 10 | 9.35 | 0.98 |
| HIV-infected symptomatic patients + +MLc (chicken egg-white) hydrochloride | 9 | 11.30 | 3.57 |

Example 3

Study on the effect of intravenously administered MLc (rat) acetate in DBA/1 mice with collagen-induced arthritis. DBA/1 mice were chosen because of its many immunological and pathological similarities to human RA (rheumatoid arthritis). MLc (rat) acetate at the dose of 20 mg/Kg of body weight (quantity expressed as equivalent of rat lysozyme c), was injected intravenously to adult mice both before the induction of the arthritis or after the onset of the disease. MLc (rat) acetate, administered by parenteral route prior to disease induction, determines a significant reduction of pain and of histological severity of arthritis. By comparing the targets of the study to the analog human disease, the capacity of the selected product to reduce clinical conditions, joint swelling, and histological severity of disease, even when administered after the onset of clinical arthritis signs, is of great significance. Mononuclear cells from RA joints maintained in culture produce many cytokines with pro-inflammatory activity, including TNF-α, measured by Elisa tests. MLc acetate in vitro reduces the production of this pro-inflammatory cytokine. Mononuclear cells (106 cells per test) were activated with PHA at the concentration of 1 μg/ml as from day 1st to 5°. Then the cells were washed three times with PBS and cultured in complete medium (500 μl) in presence or absence of MLc (rat) acetate. After two days the culture supernatant was removed and tested for its content of cytokines. Table 3 confirms the decrease of TNF-α levels after intravenous administration in those lots previously treated with MLc (rat) acetate.

TABLE 3

| | CYTOKINE LEVELS (pg/ml) | | |
|---|---|---|---|
| Treatment | TNF-α | IFN-α | IL-1α |
| Without MLc (*) | 301.60 | 7.30 | 2.51 |
| +MLc (*) 0.1 mg/ml | 55.79 | 9.76 | 3.42 |
| +MLc (*) 1 mg/ml | 20.60 | 18.07 | 3.57 |

(*) MLc acetate (rat)

Example 4

Preparation of 100,000 tablets containing 300 mg of MLc hydrochloride (chicken egg-white).

Each tablet is containing:

| Ingredients | Quantity (per tablet) |
| --- | --- |
| MLc hydrochloride (chicken egg-white) | 300 mg |
| Magnesium stearate | 25 mg |
| Microcrystalline cellulose | 250 mg |
| Silicon dioxide | 15 mg |
| Sodium polycarboxymethylcellulose | 20 mg |
| Total weight | 610 mg |

The manufacturing process is carried out by direct compression of the powder mixture through the steps already known to skilled artisans to prepare tablets, using suitable rooms and equipments for this type of production.

1) 30 Kg of MLc hydrochloride (chicken egg-white) and 25 Kg of microcrystalline cellulose are placed into a suitable blender, after passing through a seive of 1.2 mm mesh; 2) to the powder mixture previously prepared 2.5 Kg of magnesium stearate, 1.5 Kg of silicon dioxide and 2.0 Kg of sodium polycarboxy-methylcellulose are added in the minor possible time in order to obtain the content uniformity; 3) the obtained mixture is stored temporarily in suitable containers, and after approval by quality control of the active ingredient content, is then transferred to the compression unit, wherein the powder is converted into tablets by direct compression, by using rotary machine with a suitable punch of the desired measure.

97,931 biconvex tablets containing each the desired quantity of MLc hydrochloride are obtained.

| | |
| --- | --- |
| Effective yield (97,931 tablets) | 97.93% |
| (Theoretical yield 100,000 tablets | 100.0%) |
| Effective mean weight | 612.50 mg |
| (Theoretical mean weight | 610.00 mg) |
| Effective mean content for each tablet | 301.60 mg of MLc hydrochloride |
| (Theoretical content for each tablet | 300.00 mg of MLc hydrochloride) |

Example 5

Preparation of 1.500 ampoules of 10 ml (15.000 ml) containing MLc hydrochloride (chicken egg-white) (concentration of 50 mg/ml of MLc hydrochloride).

1 ml of solution is containing 50 mg of MLc hydrochloride.

| Ingredients | Quantity (per ml) |
| --- | --- |
| MLc hydrochloride (chicken egg-white) | 50.0 mg |
| Sodium chloride | 8.0 mg |
| Water for injectable preparation q.s. to | 1.0 ml |

The manufacturing process is carried out through steps already known to skilled artisans for the preparation of sterile and apyrogen solutions, using suitable rooms and equipments for the production of injectable solutions.

1) In a stainless steel dissolutor about 12.0 Kg of water for injections are introduced and under constant and slow stirring 120.0 g of sodium chloride are added; 2) separately in about 4.0 Kg of solution, prepared at the previous point, 0.750 Kg of MLc hydrochloride are dissolved; 3) solution at point (2) is added to solution (1) and the total weight of 15.0 liters is yielded with the addition of water for injectable preparations; 4) the resulting solution is then filtered through sterilizing filters and introduced in suitable sterile rooms (class 100) for its automatic ripartition in glass ampoules under atmosphere of nitrogen, using the techniques already well known in the art for the industrial manufacturing of injectable preparations.

After the chemical and biological (sterility and pyrogens) controls, the obtained ampoules are submitted to the usual automatic tests in order to evidence foreign particles and the glass integrity tests for ampoules, and then suitably packed individually in cartoon boxes for the distribution and its subsequent use in human medicine. 1,421 ampoules of 10 ml (concentration of 50 mg/ml of MLc hydrochloride) are obtained with an effective yield of 94.73% (theoretical yield 1,500).

Although the foregoing invention has been described in some detail by way of illustration and examples, for purposes of clarity of understanding, it will be obvious that certain changes and modifications may be practised within the scope of the appended claims.

The invention claimed is:

1. A regime or regimen for inducing increased levels of free TNF-α (Tumor Necrosis Factor-alpha) in plasma, comprising orally administering to a mammalian organism in need of such treatment, a thus effective amount of a pegilated lysozyme c having the formula:

$$[CH_3O-(CH_2-CH_2-O)_n-CH_2-CH_2]_x-(NH)_y$$
$$\text{Lysozyme c. } (Z)m$$

wherein:
 (NH)$_y$Lysozyme c is chicken egg-white lysozyme c;
 y is the number of free amino groups of lysine molecules present in the molecule of chicken egg-white lysozyme c, and varies from 5 to 30;
 x is between 1 and y;
 n is between 5 and 1000;
 Z is a pharmaceutically acceptable acid; and
 m is between 1 and y.

2. The regime or regimen according to claim 1, wherein n in the pegilated lysozyme c is between 120 and 200.

3. The regime or regimen according to claim 1, wherein said pharmaceutically acceptable acid in the pegilated lysozyme c is hydrochloric acid.

4. The regime or regimen according to claim 1, comprising administering the pegilated lysozyme c as a pharmaceutical composition comprising said pegilated lysozyme c and an inert carrier and/or adjuvant therefor.

5. The regime or regimen according to claim 4, wherein said pharmaceutical composition is formulated for oral administration, containing from 5% to 80% by weight of said pegilated lysozyme c.

6. The regime or regimen according to claim 5, wherein said pharmaceutical composition contains from 40% to 60% of said pegilated lysozyme c.

* * * * *